(12) United States Patent
Olschewski

(10) Patent No.: US 7,282,724 B2
(45) Date of Patent: Oct. 16, 2007

(54) METHOD AND SYSTEM FOR THE ANALYSIS OF CO-LOCALIZATIONS

(75) Inventor: Frank Olschewski, Heidelberg (DE)

(73) Assignee: Leica Microsystems CMS GMBH, Wetzlar (DE)

( * ) Notice: Subject to any disclaimer, the term of this patent is extended or adjusted under 35 U.S.C. 154(b) by 0 days.

(21) Appl. No.: 10/984,627

(22) Filed: Nov. 9, 2004

(65) Prior Publication Data

US 2005/0109949 A1   May 26, 2005

(30) Foreign Application Priority Data

Nov. 26, 2003  (DE) ................. 103 55 150

(51) Int. Cl.
G01N 21/64   (2006.01)
(52) U.S. Cl. .................................... 250/458.1
(58) Field of Classification Search ............. 250/458.1
See application file for complete search history.

(56) References Cited

U.S. PATENT DOCUMENTS 6,421,553 B1* 7/2002 Costa et al. ................ 600/476
6,483,103 B2  11/2002 Engelhardt et al.
2003/0204379 A1* 10/2003 Olschewski ................. 702/189
2003/0206296 A1* 11/2003 Wolleschensky et al. ... 356/317
2003/0231825 A1  12/2003 Olschewski

FOREIGN PATENT DOCUMENTS

DE     10006800 A1   8/2001
DE     10227111 A1   12/2003

* cited by examiner

Primary Examiner—Constantine Hannaher
(74) Attorney, Agent, or Firm—Houston Eliseeva LLP

(57) ABSTRACT

A method and a system for the analysis of co-localizations of dyes present in a specimen. The fluorescence spectra of the dyes present in the specimen are determined. A tolerance region around each of the fluorescence spectra is selected. The spectra of the specimen, in which at least two dyes are present, are then acquired pixel by pixel. Those spectra that lie within the tolerance region around the fluorescence spectra are then calculated. A lambda vector is calculated for each pixel and assigned to a spectrum. Images can be displayed in accordance with the assignment to the spectra.

14 Claims, 5 Drawing Sheets

METHOD AND SYSTEM FOR THE ANALYSIS OF CO-LOCALIZATIONS

RELATED APPLICATIONS

This application claims priority of the German patent application 103 55 150.6 which is incorporated by reference herein.

FIELD OF THE INVENTION

The invention concerns a method for the analysis of co-localizations.

The invention further concerns a system for the analysis of co-localizations.

BACKGROUND OF THE INVENTION

German Patent Application DE 100 06 800.6 discloses an apparatus for the selection and detection of at least one spectral region of a spectrally spread light beam (SP module). Selection means that are embodied as sliders are provided in the spread-out light coming from the specimen to be examined, so as thereby to direct portions of the spread-out light beam onto various detectors. The signals of the detectors are then used for image generation. DE 100 06 800.6 does not disclose actuation of the sliders in such a way that rapid and reliable detection of a specific spectrum is possible.

German Patent Application DE 102 27 111.9 discloses a spectral microscope and a method for data acquisition using a spectral microscope. Methods and systems for sensing maximum information from a fluorescing microscopic specimen are encompassed, but fault-tolerant and adaptive data acquisition is not possible with this method.

When a structure reacts to more than one dye simultaneously, this is referred to as "co-localization." The analysis of co-localizations enables the user, for example, to analyze biological structures in which two (or more) stained proteins interact, or in which two structural features coincide in a very small area. When viewing a multi-dimensional histogram in which intensity frequencies from different bands are counted, each pure dye is perceived as a widened straight line ("cigar"). In the event of co-localization, the number of straight lines to be observed in the intensity frequency space is greater than the number of dyes. This state of affairs is often made apparent by sophisticated visualization upon analysis. The cytofluorogram technique introduced by Demandolx and Davoust visualizes an ensemble of two-dimensional intensities $\{\vec{I}_i\}$ (in microscopy, the pixels of an image, voxels of a volume, or a chronologically successive series thereof; in cytofluorimetry, the measurements of several samples) as a two-dimensional scatter plot that substantially represents a two-dimensional frequency distribution. An estimate of the composite probability function of the intensities $\vec{I}$ is obtained on this basis, a method that is existing art in mathematical data analysis and whose quality depends only on the size of the ensemble. With suitable color coding and graphical representation, an image of the intensity distribution is obtained in which the straight lines can be localized by the user's eye as widened tracks. The widening exists as a result of all forms of noise and any chemical influences acting in the background. The visualization technique can be performed, however, only for a maximum of three dyes, since visualization of higher-dimensional data sets is difficult and as a rule creates more cognitive problems than benefits for the user.

SUMMARY OF THE INVENTION

It is the object of the invention to create a method for separating fluorescence spectra of dyes present in a sample, with which it is possible to determine co-localizations of dyes present in the specimen without being limited by dimensionality. The stated object is achieved by way of a method comprising the steps of:
  determining the fluorescence spectra of all the dyes present in the specimen;
  indicating a tolerance region around the fluorescence spectrum of the respective individual dye;
  acquiring, pixel by pixel, spectra of the specimen, in which at least two dyes are present;
  calculating the set of acquired spectra within the tolerance region around the fluorescence spectra;
  identifying a lambda vector for each acquired pixel;
  determining the assignment of each pixel to the spectrum;
  outputting an image, assembled from the individual pixels, for each spectrum; and
  outputting at least one image for co-localizations.

A further object of the invention to create a system for separating fluorescence spectra of dyes present in a sample, with which it is likewise possible to determine co-localizations of dyes present in the specimen. The stated object is achieved by way of a system for the analysis of co-localizations of dyes present in a specimen, comprises, a microscope; a detection device that performs a pixel-by-pixel detection of the light coming from the specimen; a computer system having an input means and a memory unit, wherein the computer system identifies a lambda vector for each acquired pixel and assigns each pixel to a spectrum; and a display, on which an output of an image made up of the individual pixels for each spectrum, and an output of an image for the co-localizations, is accomplished.

As compared with the existing art, the method has the advantage that co-localizations of several dyes in one sample are determined. This is done by identifying the various fluorescence spectra of all the dyes present in the specimen. A tolerance region around each of the fluorescence spectra is defined by the user. The spectra of the specimen, in which at least two dyes are present, are then acquired pixel by pixel. Those spectra are then correlated, spectra that are located within the tolerance region around a fluorescence spectrum being classified as pure dyes. Spectra that are located outside the tolerance band are classified as co-localizations. Analysis of the data that cannot be assigned to a tolerance band can be further refined by cluster analysis. Images (original and back-calculated) can be outputted on the display in accordance with the assignment to the spectra. It remains to note that the back-calculated image data are projected onto the center point of the tolerance bands or onto the central co-localization straight lines found by cluster analysis, in order to produce an image signal that corresponds to a pure dye or an unequivocal combination of two interacting dyes.

The fluorescence spectra of all the dyes present in the specimen are determined by acquiring reference spectra of the individual dyes. Determination of the fluorescence spectra of all the dyes present in the specimen is also possible by retrieving from a database the fluorescence spectra present in the specimen. The fluorescence spectra belonging to the individual dyes are stored in the database of the computer system; upkeep of the database is performed by the user, who can fall back on experiments based on accumulated experience, and specific reference measurements necessary for his or her purposes. The image made up of the individual pixels, and the image for the co-localizations, are of course outputted on a display.

The tolerance region is defined by an upper boundary. The upper boundary can be inputted by the user. A numerical value can likewise be inputted that defines a percentage deviation for the upper and lower boundaries of a region around the fluorescence spectrum within which the measured spectrum must lie. In the multi-dimensional intensity space, this boundary defines a cone that is placed around the straight line of the dye spectrum in the hyperspace.

In a simple expression of the method, the shape of this cone is to be considered symmetrical, the definition of the cone radius being linked to a reference intensity value that defines the absolute level. One skilled in the art can effect a concrete embodiment. In a more complex variant of the method, the position of all dye spectra is utilized. Using this prior knowledge, the cone can be "dented" in systematic fashion by giving greater weight to directions in the intensity space in which dyes lie close to one another than to directions in which dyes do not lie close to one another. The actual embodiment can be arrived at heuristically or also in model-driven fashion (Bayes, maximum likelihood, entropy-based, variance analysis, fuzzy logic), although it must be noted that all these methods are ultimately heuristic. Only the general procedure is important for this patent application, without taking sides in the "religious wars" of mathematical decision techniques.

The system for the analysis of co-localizations of dyes present in a specimen encompasses a microscope; a detection device that performs a pixel-by-pixel detection of the light coming from the specimen; and a computer system having an input means, a display, and a memory unit. The computer system identifies a lambda vector or multi-color vector for each acquired pixel. Each pixel is assigned to a spectrum or a color vector, and the display outputs respectively an image made up of the individual pixels for each spectrum, and an image for the co-localizations.

The detection device serves for pixel-by-pixel detection of the light coming from the specimen, and can comprise at least one first and one second detector. If more than one detector is provided, an SP module is then provided in front of the first and the second detector.

A scanning module, with which the illuminating light can be guided pixel by pixel over or through the specimen, is provided for illumination. Also provided is a means with which a determination is made of the fluorescence spectra of all the dyes present in the specimen, by acquiring reference spectra of the individual dyes.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
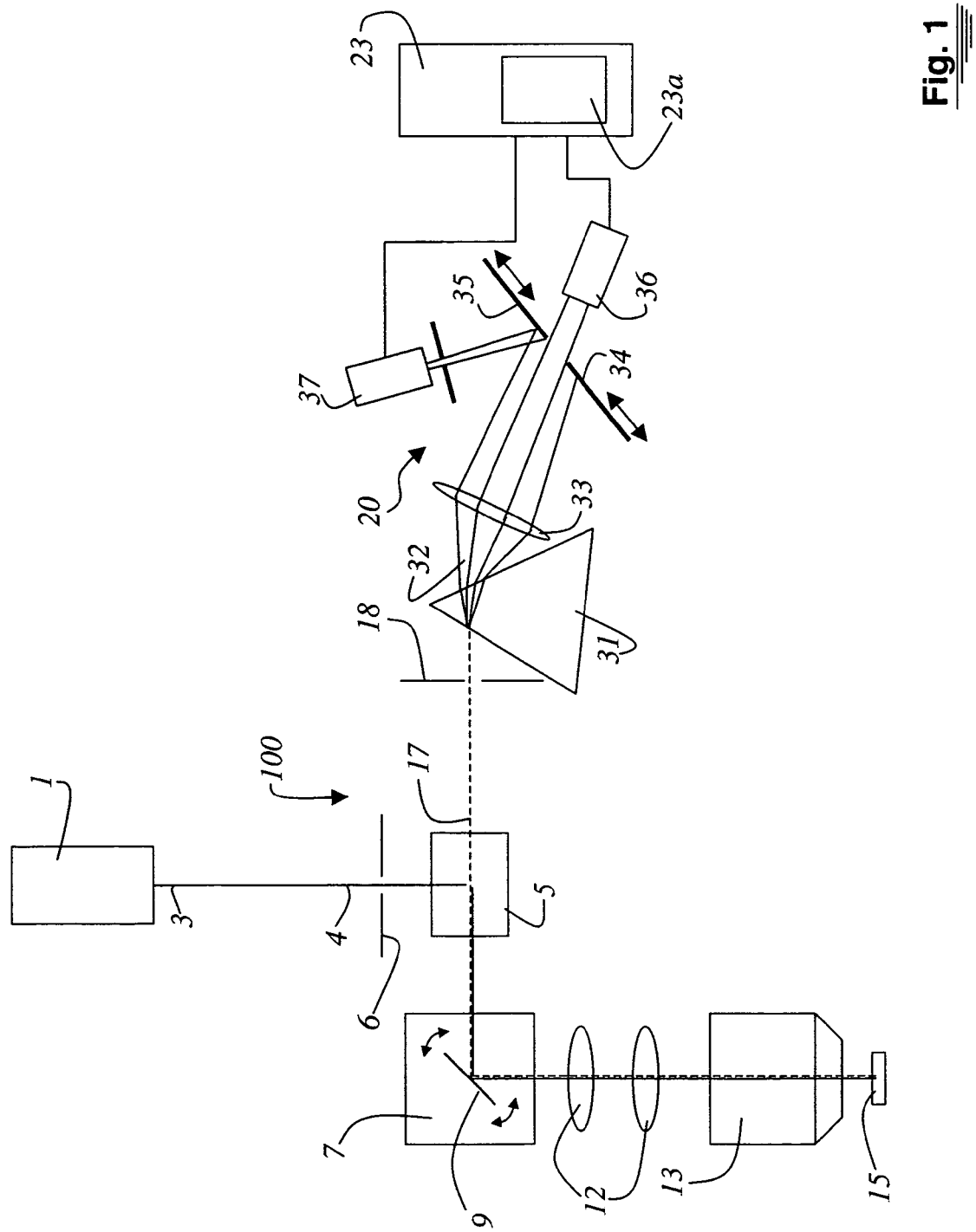
FIG. 1 schematically depicts a scanning microscope, the detector being preceded by an SP module.

FIG. 1 schematically shows the exemplary embodiment of a confocal scanning microscope 100. This is not to be construed as a limitation of the invention, however, and one skilled in the art is well aware that the same components relevant to the present invention are also installed in differently constructed microscope systems, fluorometers, and cytometers. Illuminating light 3 coming from at least one illumination system 1 is directed by a beam splitter or a suitable deflection means 5 to a scanning module 7. Illuminating light 3 passes through an illumination pinhole 6 before it strikes deflection means 5. Scanning module 7 encompasses a gimbal-mounted scanning mirror 9 that guides illuminating light 3, through a scanning optical system 12 and a microscope optical system 13, over or through a specimen 15. In the case of non-transparent specimens 15, illuminating light 3 is guided over the specimen surface. With biological specimens 15 (preparations) or transparent specimens, illuminating light 3 can also be guided through specimen 15. For these purposes, non-luminous preparations are, if applicable, prepared with one or more suitable dyes (not depicted, since this is established existing art). The dyes present in specimen 15 are excited by illuminating light 3 and emit light in a characteristic region of the spectrum peculiar to them. The spectra of the various dyes are superimposed, and the task is then to adjust scanning microscope 100 so as to make possible separation and thus detection of the individual dyes present in specimen 15.

The light proceeding from specimen 15 is a detected light 17. The latter travels through microscope optical system 13 and scanning optical system 12 and via scanning module 7 to deflection means 5, traverses the latter, and travels via a detection pinhole 18 onto at least one detector 36, 37 that is embodied as a photomultiplier. It is clear to one skilled in the art that other detection components, for example diodes, diode arrays, photomultiplier arrays, CCD chips, or CMOS image sensors, can also be used. Detected light 17 proceeding from or defined by specimen 15 is depicted in FIG. 1 as a clashed line. In detectors 36, 37, electrical detected signals proportional to the power level of the light proceeding from specimen 15 are generated. Because, as already mentioned above, light having a characteristic spectrum is emitted from specimen 15, it is useful to provide an SF module 20 in front of the at least one detector 36, 37. The data generated by the at least one detector 36, 37 are conveyed to a computer system 23. At least one peripheral device is associated with computer system 23. The peripheral device can be, for example, a display on which the user receives instructions for setting scanning microscope 100 or can view the current setup and also the image data in graphical form. Also associated with computer system 23 is an input means that comprises, for example, a keyboard, an adjusting apparatus for the components of the microscope system, and a mouse.

SP module 20 (IZIG. 2 ) is embodied in such a way that it can acquire a complete lambda scan, i.e. all ti-ia wavelengths proceeding from specimen 15 are recorded. In other words, a complete wavelength range is acquired in order thereby to sense all the waves proceeding from a specimen. The data are transferred to computer system 23 and can then be displayed on display 23a in a manner that can be determined by the user. Detected light 17 is spatially spectrally divided with a prism 31. A further possibility for spectral division is the use of a reflection or transmission grating. The spectrally divided light fan 32 is focused with focusing optical system 33 and then strikes a mirror aperture arrangement 34, 35. Mirror aperture arrangement 34, 35, the means for spectral spatial division, focusing optical system 33, and detectors 36 and 37 are together referred to as SP module 20 (or die multi-band detector).

Figure 2:
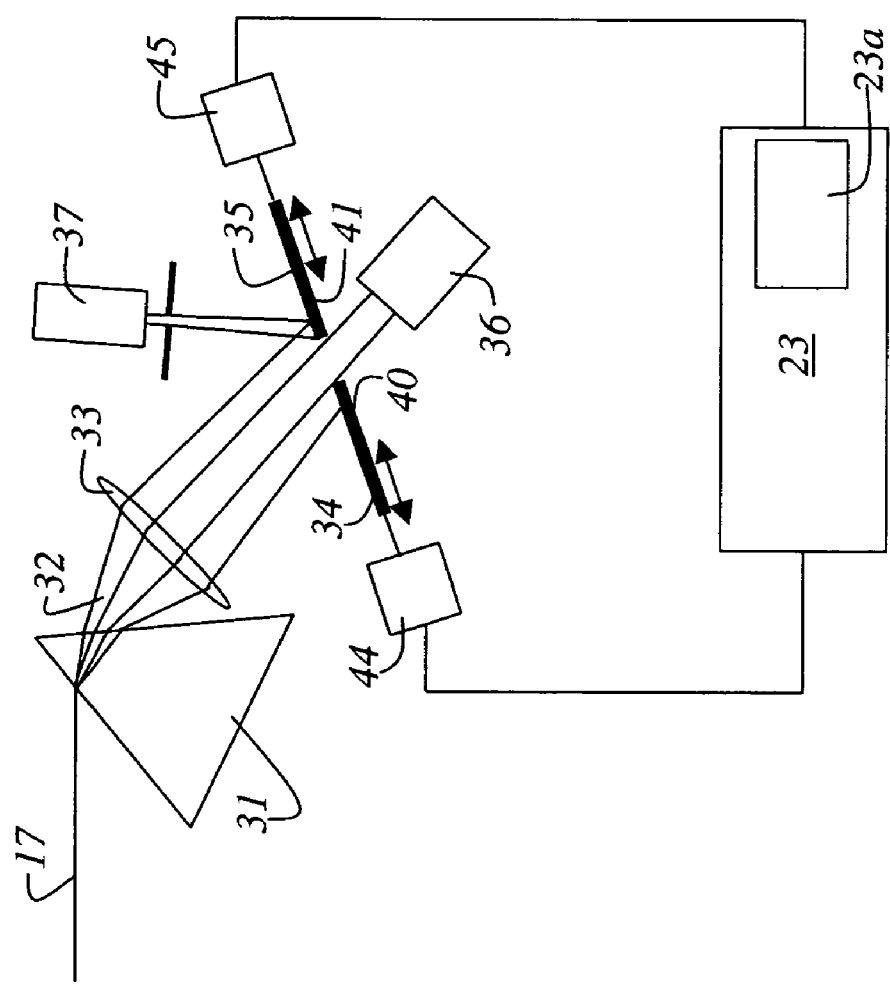
FIG. 2 schematically depicts the SP module in detail.

As is evident from FIG. 2, a desired portion of the spectrum of detected light 17 can be picked out or systematically selected by means of mirror aperture arrangement 34, 35. In the exemplary embodiment depicted here, the mirror aperture arrangement 34, 35 or slit aperture arrangement equipped with a first and a second slider 40 and 41. It is self-evident that for the selection of more than two spectral regions, a corresponding number of sliders must be provided. A corresponding increase in the mirror sliders results directly in an increase in the spectral bands to be sensed concurrently. A first motor 44 is associated with first slider 40, and a second motor 45 with second slider 41. Motors 44 and 45 permit a displacement, described in accordance with the method below, of sliders 40 and 41. As a result of the displacement of sliders 40 and 41, only a portion of the divided light fan 32 of detected light 17, containing only light of the preselected spectral region, passes through mirror aperture arrangement 34, 35 and is detected by detector 36, which is embodied as a photomultiplier. Another portion of the divided light fan 32 is reflected at mirror aperture arrangement 35 and arrives at detector 37, which is also embodied as a photomultiplier. A spectral scan of specimen 15 can be performed by suitable shifting of mirror aperture arrangement 35. The result obtained is data in the form of a field $\vec{I}(x,y,z,t)$, the individual pixels containing an n-dimensional vector of spectral measurements $$\vec{I}(x_0, y_0, z_0, t_0) = \begin{pmatrix} I([\lambda_1 \ldots \lambda_2]) \\ I([\lambda_3 \ldots \lambda_4]) \\ \ldots \\ I([\lambda_{2n-1} \ldots \lambda_{2n}]) \end{pmatrix}.$$

Illuminating light 3 is guided through scanning module 7 and over or through specimen 15. Specimen 15 is thus illuminated in point-by-point or pixel-by-pixel fashion, and thereby also detected in the same fashion. If there are two dyes, all the observations then lie in one plane and the tracks of the individual spectra each lie on one straight line in the two-dimensional space extending between the two dye reference vectors. For n dyes, the individual spectra lie on straight lines in the n-dimensional space. Three dyes result in a volume, four in a hypervolume, etc.

Figure 3:
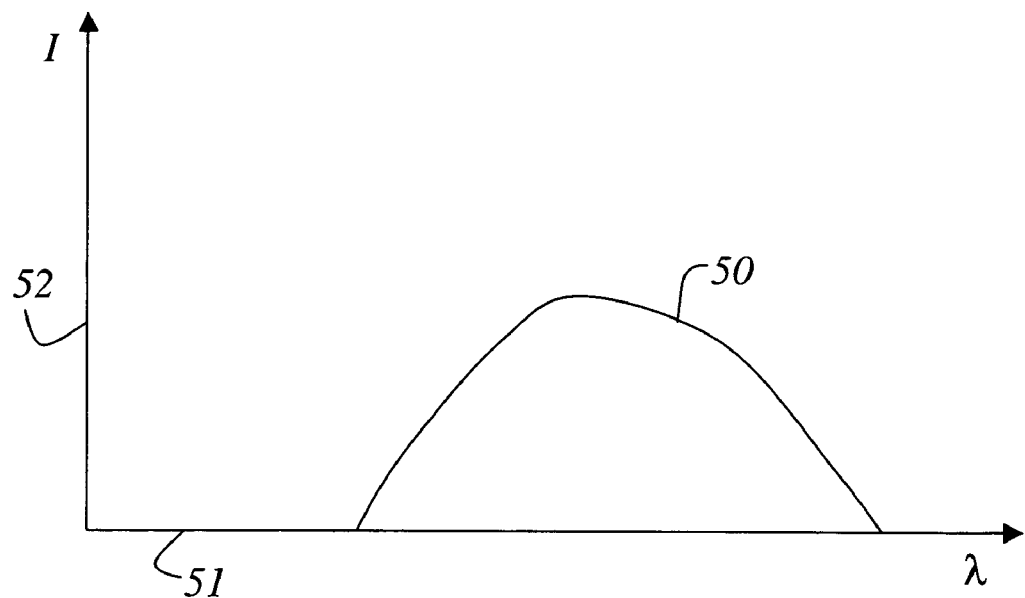
FIG. 3 schematically depicts the fluorescence spectrum of a dye that is present in the sample.

FIG. 3 depicts, by way of example, a spectrum 50 of a dye. The wavelength λ of the light proceeding from the specimen or from a pixel of the specimen is plotted on abscissa 51. The intensity of the fluorescent light proceeding from the specimen is plotted on ordinate 52. Spectrum 50 depicted in FIG. 3 can be obtained by the user, for example, from a database that is implemented in computer system 23. The user can also determine spectrum 50 him- or herself by way of a reference measurement on the particular dye. The image also, if applicable, corresponds to the measured signal at a measurement point or pixel at which that specific dye is present in pure fashion.

Figure 4:
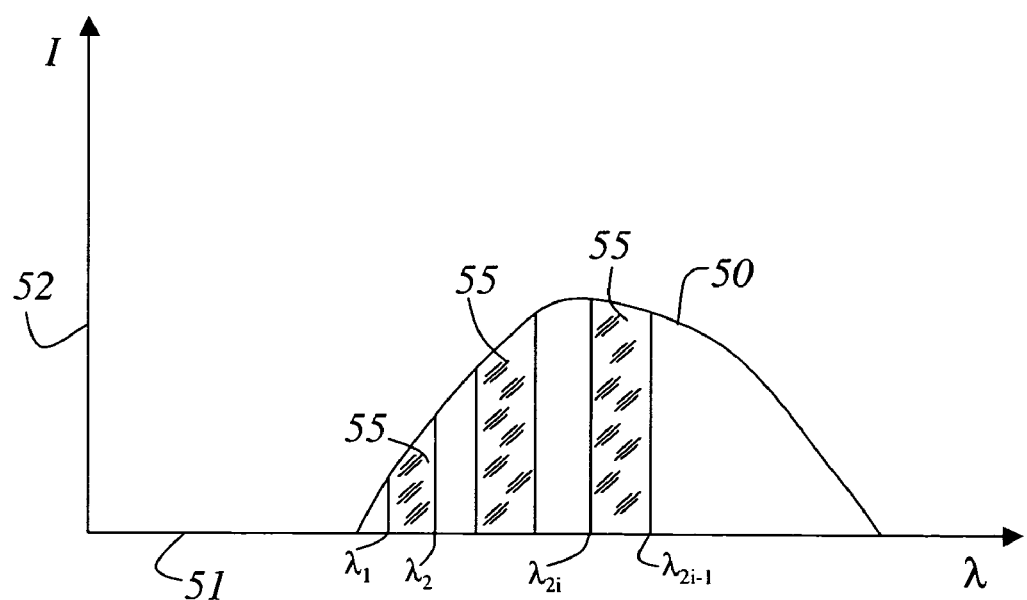
FIG. 4 depicts, by way of example, the calculation of a directional vector based on the spectrum of FIG. 3.

Spectrum 50 can be converted, in the n-dimensional space, directly into a directional vector if the integration regions as depicted in FIG. 4 are known and determined. For each spectral band 55, the area under the emission spectrum can be determined as follows:

$$a_i = \int_{\lambda_{2i-1}}^{\lambda_{2i}} \varepsilon(\lambda) d\lambda.$$

The individual results $a_i$ can be combined into a directional vector $$\vec{a} = \begin{pmatrix} a_1 \\ a_2 \\ \ldots \\ a_n \end{pmatrix};$$

not all wavelengths necessarily need to be measured, since gaps and overlaps do not interfere with the method.

Figure 5:
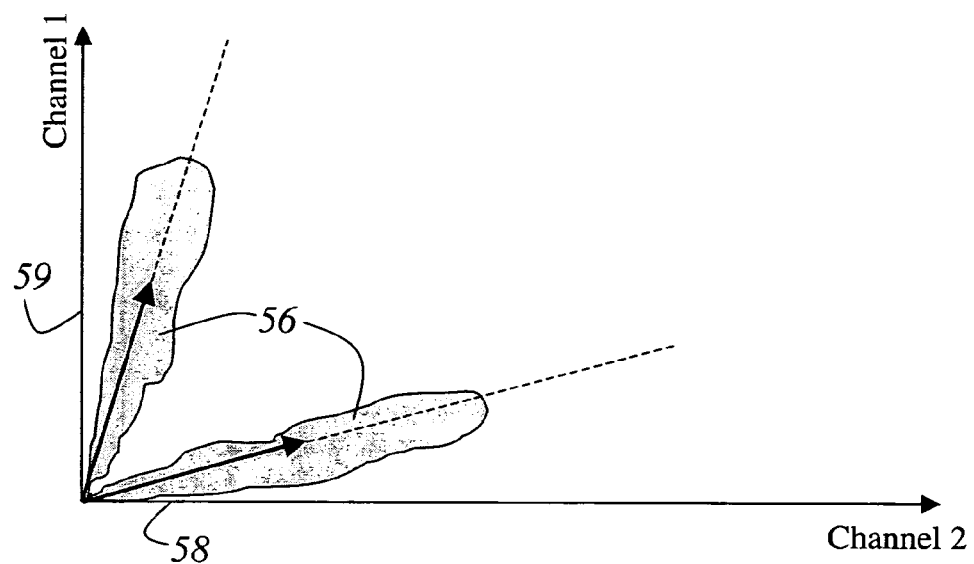
FIG. 5 graphically depicts, in a two-dimensional intensity histogram, the spatial separation of fluorescence spectra of two dyes present in the sample.
Figure 6:
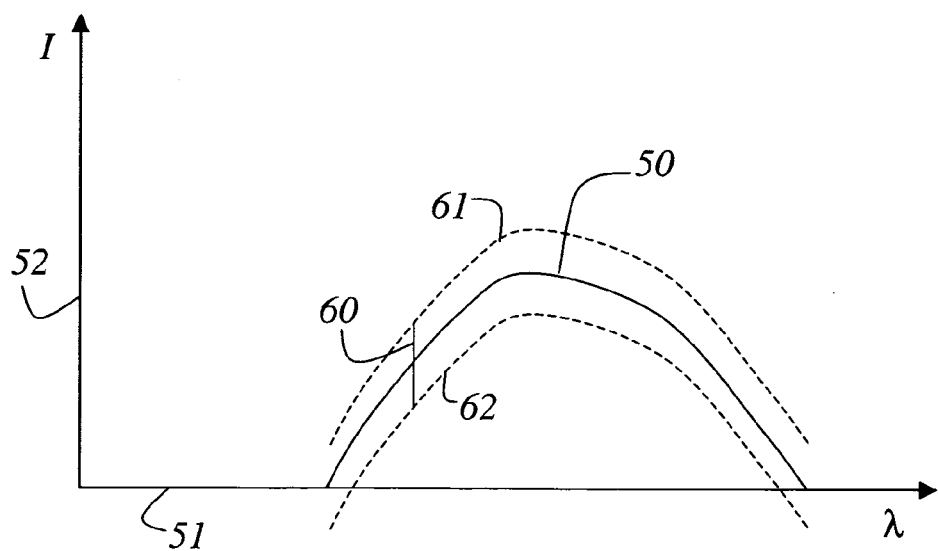
FIG. 6 graphically depicts a tolerance region, defined around the fluorescence spectrum of FIG. 3, that corresponds in the intensity histogram to a cone about the center point of the "cigar"

FIG. 5 graphically depicts the spatial separation of fluorescence spectra of two dyes present in the specimen. In the two-dimensional case, the spectra of the two dyes can be displayed on a peripheral device as lobes 56 in an intensity histogram presentation, the intensity of the first channel being depicted on abscissa 58, and the intensity of the second channel on ordinate 59. The problem is co-localizations. Co-localizations are pixels of the acquired image of a sample in which both dyes (as is relevant for the two-dimensional case) occur simultaneously. These form islands in the intensity histogram between lobes 56, and are difficult to separate from, or assign to, those lobes. In the two-dimensional case, graphical solutions exist that define, by way of figures drawn interactively by the user, a region of interest (ROI) that can be used for marking, classification, and sorting. For the case of more than two dimensions, a solution is disclosed in FIG. 6, which is a graphical depiction of a tolerance region defined around fluorescence spectrum 50 of FIG. 3. The tolerance region thus defines a region 60 around fluorescence spectrum 50 within which a tolerable variation of the spectrum is possible. The usa can define the variation by indicating tolerances. The example shown in FIG. 6 illustrates the situation in which, for example, 10% variation is tolerated, referring to an intensity (e.g. maximum, avenge) of the image. The concrete embodiment is a degree of freedom of the method, and is left to the implementation abilities of one skilled in the art. An upper boundary 61 and a lower boundary 62, which are derived automatically from the variation, thus characterize region 60 within which a measured spectrum must or can lie so that it is assigned to the selected dye.

Figure 7:
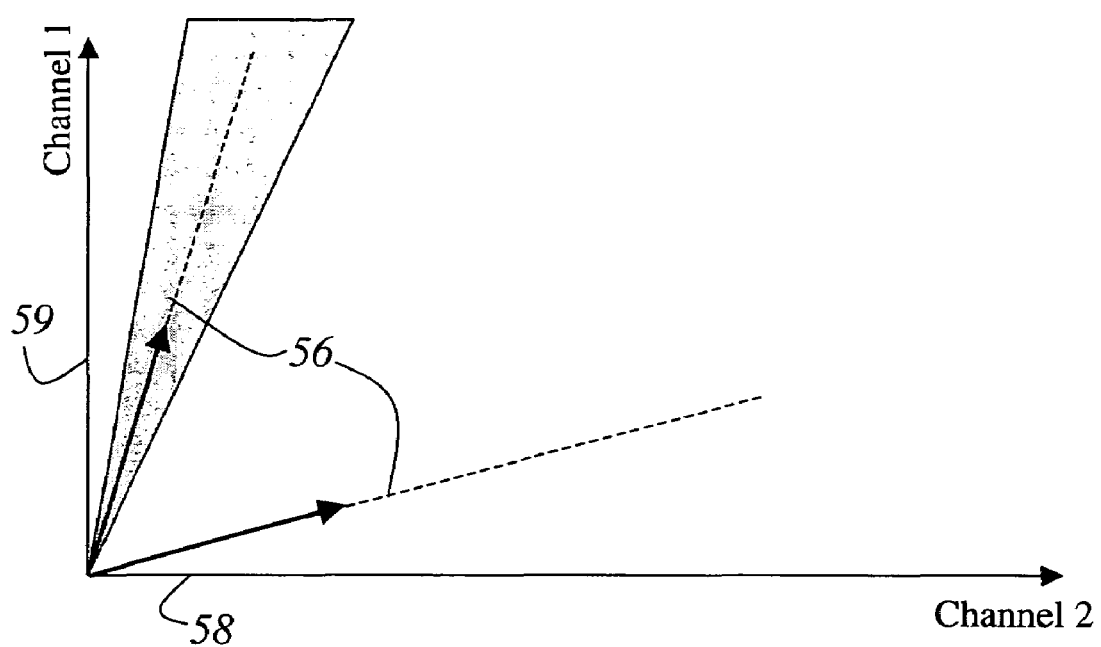
FIG. 7 depicts the classification of fluorescence spectra of dyes present in the sample, the tolerance region of FIG. 6 being employed for separation.

FIG. 7 depicts the spatial separation of fluorescence spectra of dyes present in the specimen. The spectra are depicted as vectors, and the tolerance region is utilized for separation. For calculation of the tolerance bands, firstly a reference spectrum is inputted. The reference spectrum can be retrieved from a database. The reference spectrum can also be acquired by the user him- or herself, by the fact that the user measures the fluorescence spectrum of the pure dye. The term "pure dye" is understood to mean that the fluorescence spectrum of the dye only is measured. At the least, however, the determination of the fluorescence spectrum is to be made without the influence of one or more further dyes. The user can define a tolerance region. It is also conceivable for the system to suggest a tolerance region to the user. Based on the tolerance region, the tolerance spectra are calculated for each individual spectrum. From the data acquired by the scanning microscope, the set of spectra lying within the tolerance bands is calculated. In this context, of course, each tolerance spectrum must be contained in that set.

What is claimed is:

1. A method for analysis of co-localizations of at least two dyes present in a specimen comprising the following steps:
    determining a reference fluorescence spectrum vector of each of the dyes, respectively;
    determining a tolerance region around the reference fluorescence spectrum vector of each of the dyes, respectively;
    acquiring, pixel by pixel, acquired pixel spectra of the specimen;
    for each pixel spectrum determining a pixel lambda vector;
    displaying an image formed of the acquired pixels having pixel lambda vectors within each tolerance region; and
    displaying a graphical image of co-localizations by determining which pixels have pixel lambda vectors outside of the tolerance regions.

2. The method as defined in claim 1, wherein the reference fluorescence spectrum vector of each of the dyes is determined by acquiring reference spectrum of each dye, respectively.

3. The method as defined in claim 1, wherein the determination of the reference fluorescence spectrum vector of each of the dyes present in the specimen is accomplished by retrieving from a database the reference fluorescence spectrum vector of each of the dyes present in the specimen.

4. The method as defined in claim 3, wherein the fluorescence spectrum vector of each of the dyes is stored in the database of a computer system.

5. The method as defined in claim 1, wherein the acquiring of the spectra from the specimen is performed with an SP module.

6. The method as defined claim 1, wherein an image corresponding to the individual pixels and at least one graphical image of the co-localizations are displayed.

7. The method as defined in claim 1, wherein the tolerance region is defined by an upper boundary and a lower boundary.

8. The method as defined in claim 7, wherein the upper boundary and lower boundary are defined by a user, and optionally experience a refinement by way of a discriminance analysis among all the dyes present.

9. A system for analysis of co-localizations of dyes present in a specimen comprising:
    a microscope;
    a detection device that performs a pixel-by-pixel detection capable of detecting light coming from the specimen;
    a computer system having an input means and a memory unit, wherein the computer system is capable of identifying a lambda vector for each acquired pixel and assigns each pixel to a spectrum;
    and a display, on which an output of an image made up of the individual pixels for each spectrum, and an output of an image for the co-localizations, is accomplished.

10. The system as defined in claim 9, wherein for pixel-by-pixel detection of the detected light coming from the specimen, the detection device comprises at least one first and one second detector; and an SP module is provided in front of the first and the second detector.

11. The system as defined in claim 10, wherein a scanning module is provided that guides illuminating light pixel by pixel over or through the specimen.

12. The system as defined in claim 9, wherein a means is provided with which a determination is made of the fluorescence spectra of all the dyes present in the specimen, by acquiring reference spectra of the individual dyes.

13. The system as defined in claim 9, wherein the memory unit encompasses a database in which are stored fluorescence spectra of various dyes that the user retrieves based on presence in the specimen.

14. The system as defined in claim 9, wherein a means is provided with which a tolerance region is inputtable for each fluorescence spectrum of a dye.

* * * * *